United States Patent
Van Der Merwe et al.

(10) Patent No.: US 7,129,082 B2
(45) Date of Patent: Oct. 31, 2006

(54) BIO-REACTOR DEVICE

(75) Inventors: Schalk Van Der Merwe, Pretoria (ZA); Francis Sean Moolman, Pretoria (ZA); Robert Paul Bond, Pretoria (ZA); Adriaan Jacobus Van Wyk, Pretoria (ZA)

(73) Assignee: CSIR, Pretoria (ZA)

( * ) Notice: Subject to any disclaimer, the term of this patent is extended or adjusted under 35 U.S.C. 154(b) by 476 days.

(21) Appl. No.: 10/380,482

(22) PCT Filed: Aug. 27, 2001

(86) PCT No.: PCT/IB01/01549
§ 371 (c)(1),
(2), (4) Date: Mar. 12, 2003

(87) PCT Pub. No.: WO02/22775
PCT Pub. Date: Mar. 21, 2002

(65) Prior Publication Data
US 2003/0180942 A1    Sep. 25, 2003

(30) Foreign Application Priority Data
Sep. 13, 2000    (ZA)    ..................... 00/4861

(51) Int. Cl.
C12M 1/12    (2006.01)

(52) U.S. Cl. ............ 435/297.2; 422/45; 422/46; 422/48; 210/645; 210/646

(58) Field of Classification Search ............. None
See application file for complete search history.

(56) References Cited

U.S. PATENT DOCUMENTS 5,510,262 A    4/1996    Stephanopoulos et al.
6,759,245 B1 *    7/2004    Toner et al. ............. 435/401

FOREIGN PATENT DOCUMENTS

| WO | 86/05811 | 10/1986 |
| WO | 94/01530 | 1/1994 |
| WO | 95/27041 | 10/1995 |

* cited by examiner

Primary Examiner—David Redding
(74) Attorney, Agent, or Firm—Merchant & Gould P.C.

(57) ABSTRACT

The invention provides a bio-reactor device and a method of cultivating live cells. The device comprises a holder which contains a matrix of porous foam material in whose interior live cells are anchored, the device comprising also a liquid contained in the holder. The liquid is an oxygen carrier and saturates the matrix, the liquid comprising a synthetic or semi-synthetic constituent. The method involves perfusing the oxygen carrier liquid through the matrix to deliver oxygen to the cells and to absorb carbo-dioxide from the cells.

16 Claims, 1 Drawing Sheet

BIO-REACTOR DEVICE

THIS INVENTION relates to a bio-reactor device. The invention also relates to a method of cultivating live cells.

According to the invention there is provided a bio-reactor device which comprises a holder containing a three-dimensional matrix of open-cell foam material, the foam material having a porous interior and containing, in its porous interior and anchored thereby, live cells, the bio-reactor device also comprising a liquid contained in the holder, which liquid is an oxygen carrier and which saturates and immerses the matrix, the liquid comprising, at least in part, a synthetic or semi-synthetic oxygen-carrying constituent, the matrix being a unitary or integral continuous mass of the foam material, the foam material being an open-cell foam material and the device forming part of an oxygen carrier liquid circulation arranged for circulation of oxygen carrier liquid into the holder, for circulation of said liquid by perfusion through the matrix in which the live cells are cultivated, and for circulation thereof out of the holder.

By synthetic is meant that the oxygen carrying constituent is made by an artificial process with no biological process steps, semi-synthetic meaning that the constituent is artificially synthesized from biologically produced starting materials.

The open-cell foam material may be bio-compatible and bio-stable, being a polymeric foam material. Thus, the foam material may be a foam of a polymer selected from the group consisting of polyurethane polymers, polyvinyl chloride polymers, polyethylene polymers, polypropylene polymers, polystyrene polymers, copolymers of the aforegoing, styrene-butadiene copolymers, styrene-acrylonitrile copolymers, acrylonitrile-butadiene-styrenecopolymers, poly(methyl methacrylate) polymers, polyamide polymers, poly(hexamethylene adipamide) polymers, poly(hexamethylene sebacamide) polymers, polycapralactone polymers, poly(ethylene terephthalate) polymers, poly(butylene terephthalate) polymers, polycarbonate polymers, polyacetal polymers, polyvinyl alcohol polymers, urea formaldehyde polymers, fluorine-containing polymers, silicone-containing polymers, and mixtures of the aforegoing polymers and copolymers.

As indicated above, the mattix is a unitary or integral continuous mass of the foam material.

The live cells may be animal cells, in particular mammalian cells, the oxygen carrier liquid forming a blood substitute which also acts as a carbon dioxide carrier. In use, as described in more detail hereunder, the oxygen carrier liquid is perfused through the bio-reactor device and through the matrix in the device, where the live cells absorb oxygen from the oxygen carrier liquid and where the oxygen carrier liquid absorbs carbon dioxide produced by the cells. Thus, although the oxygen carrier liquid has as an important function the carrying of oxygen, this is not is sole function, and it will also act as a carbon dioxide carrier and will have other functions, as described hereunder. More particularly, the oxygen carrier liquid may comprise an aqueous liquid, the oxygen carrier liquid having, as the synthetic or semi-synthetic oxygen-carrying constituent, at least one member selected from the group consisting of cell-free haemoglobins, cross-linked haemoglobins, liposome-encapsulated haemoglobins and perfluorocarbons, preferably perfluorocarbons. The synthetic or semi-synthetic constituent may be a perfluorocarbon, the oxygen carrier liquid being an emulsion of an organic phase and an aqueous phase, the organic phase comprising the perfluorocarbon and typically being the disperse phase of the emulsion, and the aqueous phase being the continuous phase of the emulsion and comprising the aqueous liquid, the aqueous phase typically comprising blood plasma. Instead, the synthetic or semi-synthetic constituent may be a cell-free haemoglobin, the cell-free haemoglobin being dissolved in the aqueous liquid, such as blood plasma. Instead, the synthetic or semi-synthetic constituent may be liposome-encapsulated haemoglobin, the liposome-encapsulated haemoglobin being suspended as a suspension thereof in the aqueous liquid, such as blood plasma. The term oxygen carrier liquid is thus intended to include such emulsions, solutions and suspensions, in which the synthetic or semi-synthetic constituent is dispersed, by emulsification, dissolution or suspension thereof in an aqueous liquid such as blood plasma.

The holder may be a reaction vessel or container having an oxygen carrier liquid inlet, conveniently at a high level, and an oxygen carrier liquid outlet, conveniently at a low level, the oxygen carrier liquid outlet being at a lower level than the oxygen carrier liquid inlet and forming a low level oxygen carrier liquid drain, the holder optionally being provided with a temperature regulation device for regulating the temperature of the matrix and of the oxygen carrier liquid, for example a heating/cooling jacket having an inlet and an outlet for a heating/cooling liquid such as water. The device may thus form part of a temperature regulating liquid circuit for circulating a temperature regulating liquid to and away from the holder, the holder being provided with a temperature regulation device in the form of a hollow temperature regulating jacket for the holder, the jacket having an inlet and an outlet for a temperature regulating liquid, the temperature regulating circuit comprising a liquid circulation device for circulating the temperature regulating liquid along and around the temperature regulating circuit, a thermostat, and a heat transfer device remote from the holder and operative in response to signals from the thermostat to control the temperature of the temperature regulating liquid and hence to regulate the temperature of the matrix and of the oxygen carrier liquid. Instead, the whole apparatus or installation may be contained in a temperature-regulated environment.

The bio-reactor device may form part of a portable apparatus, or may form part of a fixed installation, to which apparatus or installation the invention accordingly extends. In such apparatus or installation the bio-reactor device, as indicated above, forms part of an oxygen carrier liquid circulation circuit arranged to circulate oxygen carrier liquid into the holder, e.g. via its inlet, through the matrix in which the live calls are anchored, and out of the holder, e.g. via its outlet. The apparatus or installation may also optionally include a toxin-removal device, such as an absorption column or an ion-exchange unit.

The oxygen carrier liquid circulation circuit may include at least one device which is selected from the group consisting of liquid circulation devices such as pumps for circulating the oxygen carrier liquid along and around the circuit, biomass removal devices such as filters for removing biomass from oxygen carrier liquid issuing from the holder, separation devices for separating the synthetic or semi-synthetic constituent of the oxygen carrier liquid from the other constituents thereof, carbon dioxide removal devices for removing carbon dioxide from the oxygen carrier liquid, oxygenation devices for oxygenating the oxygen carrier liquid, and de-aeration devices for de-aerating the oxygen carrier liquid. In a particular embodiment the circulation circuit may include a plurality of the devices of the group, the devices being arranged, starting with the holder, in a sequence which comprises a single biomass removal device, followed in turn by a single separation device, a single carbon dioxide removal device, a single oxygenation device, a single de-aeration device and a single liquid circulation device, the holder following the liquid circulation device so that the circuit is an endless or closed circuit, and the liquid circulation device being arranged to circulate the oxygen carrier liquid along and around the circuit in the direction in which the devices of the group follow one another in said sequence. In such case and when the oxygen carrier liquid is an emulsion containing a perfluorocarbon as its synthetic constituent emulsified with an aqueous liquid such as blood plasma, perfluorocarbon will be separated physically by the separation device from the plasma, and from any growth medium present, for example by centrifugation or filtration, optionally after the emulsion has been broken; but for other synthetic constituents, such as cell-free haemoglobin or liposome-encapsulated haemoglobin, other separation techniques, tailored to the synthetic oxygen carrier constituents in question, can be used; and a further function of this separation device is that it can act as a reservoir for the liquid of the plasma circulation circuit. As indicated above, in a particular arrangement the plasma circulation circuit contains all of the devices listed above, and in this case they may follow one another in series in the sequence specified above, in the direction of flow along the circuit, the pump being immediately upstream of the bio-reactor device, and the biomass filter immediately downstream of the bio-reactor device. In other words, the sequence comprises, in said direction of flow and starting with the bio-reactor device, the biomass removal device followed in turn by the separation device, the carbon dioxide removal device, the oxygenation device, the de-aeration device and the pump, the bio-reactor device following the pump. The carbon dioxide removal device and the oxygenation device can optionally be a single device.

As indicated above, the apparatus or installation may include a heating/cooling liquid circuit for circulating heating/cooling liquid through the heating/cooling jacket, this circuit optionally having its own liquid circulation device such as a pump, a thermostat in the jacket and liquid heating/cooling means remote from the bio-reactor device and operative in response to signals from the thermostat, the thermostat conveniently comprising a thermocouple connected to a programmable logic controller.

The apparatus or installation may include a blood circulation circuit, e.g. for receiving or withdrawing blood from a human patient or an animal, for circulating the blood into contact with the plasma circulation circuit to deliver blood constituents such as blood plasma to the oxygen carrier liquid, and for receiving or withdrawing aqueous constituents of the oxygen carrier liquid and returning them to the patient. The blood circulation circuit may include a liquid circulation device such as a pump for circulating blood and blood constituents around and along the blood circulator circuit; a plasma separation device for separating blood from the patient into a blood plasma fraction which is free of blood cells and a blood cell-containing fraction containing the blood cells and a residual part of the plasma; and a de-aeration device. The plasma separation device may optionally include a further device, such as a blood filter. The sequence of the devices forming part of the blood circulation circuit may be in the sequence in which they are listed above, in the direction of flow of liquid along and around the circuit. Thus, starting with the patient, the first device may be the pump, followed in turn by the plasma separation device and the de-aeration device, the de-aeration device being followed by the patient. In other words, the oxygen carrier liquid circulation circuit may be connected to a blood circulation circuit for circulating blood into contact with oxygen carrier liquid in the oxygen carrier liquid circulation circuit, for delivering cell-free blood constituents to the oxygen carrier liquid circuit, and for receiving or withdrawing cell-free aqueous oxygen carrier liquid constituents from the oxygen carrier liquid circuit, the blood circulation circuit including a blood circulation device for circulating blood along and around the blood circulation circuit, a plasma separation device for separating blood circulating along and around the blood circulation circuit into a cell-free blood plasma fraction and a blood cell-containing fraction containing blood cells and some blood plasma, and a de-aeration device for de-aerating blood circulating along and around the blood circulation circuit. As indicated above, the devices of the blood circulation circuit may be arranged in a sequence, in which sequence the blood circulation device is followed in turn by the plasma separation device and the de-aeration device, the blood circulation device being arranged to circulate blood along and around the blood circulation circuit in the direction in which the devices of the blood circulation circuit follow one another in said sequence.

The plasma separation device may be connected to the plasma circulation circuit, such that the plasma separation device is arranged to feed plasma from the patient's blood into the plasma circulation circuit, conveniently downstream of the de-aeration device of the plasma circulation circuit and upstream of its pump and bio-reactor device; and the separation device of the plasma circulation circuit may be connected to the blood circulation circuit in a fashion such that the separation device is arranged to feed the aqueous liquid separated from the oxygen carrier liquid into the blood circulation circuit, conveniently downstream of the plasma separation device and upstream of the de-aeration device of the blood circulation circuit. In other words the connection between the oxygen liquid circulation circuit and the blood circulation circuit may be a connection between the oxygen carrier liquid circulation circuit and the plasma separation device of the blood circulation circuit.

The apparatus or installation conveniently includes one or more of a nutrient make-up flow line, an oxygen carrier liquid make-up flow line and an oxygen feed line (which oxygen feed line may be for feeding oxygen or a blend of oxygen and other gases such as carbon dioxide), each feeding into the oxygenation device of the plasma circulation circuit; and the apparatus or installation may include one or more of a vacuum line for withdrawing carbon dioxide from the carbon dioxide removal device and connected thereto, and a biomass flow line, connected to the biomass removal device, for discharging, to waste, biomass removed by the biomass removal device from the oxygen carrier liquid. The installation may also include a blood-conditioning feed line for feeding blood-conditioning substances into the plasma circuit, eg to control pH or to correct other chemical imbalances and conveniently feeding into the oxygenation device.

The invention extends to a method of cultivating live cells, the method comprising circulating a liquid which is an oxygen carrier and which comprises, at least in part, a semi-synthetic or synthetic oxygen-carrying constituent, through a matrix of foam material having a porous interior in which live cells are anchored, the matrix forming part of an oxygen carrier liquid circulation circuit arranged for circulation of oxygen carrier liquid, into a holder containing the three-dimensional matrix, through the matrix, and out of the holder, the cells absorbing oxygen and nutrients from the liquid and the liquid absorbing carbon dioxide and other metabolic products from the cells, the matrix being a unitary or integral mass of open-cell foam material, and the circulating of the oxygen carrier liquid through the matrix being by perfusing the oxygen carrier liquid through the matrix.

The matrix may form part of a bio-reactor device which may, in more detail, be as described above; and the oxygen carrier liquid may in turn be as described above with reference to the apparatus or installation of the invention. Naturally, the live cells will absorb constituents of the oxygen carrier liquid other than oxygen, such as nutrients, and the oxygen carrier liquid will absorb metabolic products of the cells other than carbon dioxide.

The bio-reactor device may, as indicated above, form part of an apparatus or installation as described herein, so that perfusing the liquid through the matrix is by circulating the liquid along and around an oxygen carrier liquid circulation circuit, such as a plasma circulation circuit, and through the matrix in the holder, the method optionally including one or more of the steps of:

controlling the temperature of the matrix and the interior of the holder of the bio-reactor device by monitoring the temperature therein and circulating a heating/cooling liquid along the heating/cooling liquid circuit at an appropriate flow rate and temperature to keep the temperature of the matrix and interior of the holder within a desired range of values;

filtering biomass from the oxygen carrier liquid by means of a biomass filter and discharging it to waste along the biomass flow line;

separating the oxygen carrier liquid into an aqueous phase such as a plasma phase and a synthetic constituent-containing phase such as an organic polyfluorocarbon phase in the separation device, while feeding the separated synthetic constituent-containing phase along the plasma circulation circuit and feeding the separated aqueous phase into the blood circulation circuit;

removing carbon dioxide from the oxygen carrier liquid by means of the carbon dioxide removal device, the removed carbon dioxide being withdrawn from the carbon dioxide removal device along the vacuum line;

oxygenating the oxygen carrier liquid in the oxygenation device and optionally feeding nutrient make-up, oxygen carrier liquid make-up and blood-conditioning substances into the oxygen carrier liquid in the oxygenation device; and de-aerating the oxygen carrier liquid in the de-aeration device in the plasma circulation circuit, the oxygen carrier liquid being circulated around and along the plasma circulation circuit by the pump.

In particular, the oxygen carrier liquid may comprise an aqueous constituent in the form of blood plasma, perfusing the liquid through the matrix being by circulating the liquid along and around an oxygen carrier liquid circulation circuit and through the matrix, and the method including the step of regulating the temperature of the matrix and oxygen carrier liquid, to keep the temperature of the matrix and oxygen carrier liquid within a desired range of values. In this case, the method may include the step of removing biomass from the oxygen carrier liquid circulating along and around the oxygen carrier liquid circuit and discharging the removed biomass to waste. The method may also include separating the oxygen carrier liquid circulating along and around the oxygen carrier liquid circuit into an aqueous phase and a semi-synthetic or synthetic oxygen-carrying constituent-containing phase, the aqueous phase being substantially free of said oxygen-carrying constituents, and the method including retaining the separated semi-synthetic or synthetic constituent-containing phase in the oxygen carrier liquid circulation circuit and feeding the separated aqueous phase into a blood circulation circuit connected to the oxygen carrier liquid circulation circuit.

The method may include treating the blood of a patient, so that it may include one ore more of the steps of:

withdrawing blood from a patient, in particular veinous blood;

separating the blood into a plasma fraction and a cell-containing fraction, the plasma fraction being fed into the oxygen carrier liquid in the plasma circulation circuit while the cell-containing fraction is returned to the patient (together with separated plasma phase from the plasma circulation circuit as described hereunder);

de-aerating the cell-containing fraction before it is returned to the patient; and feeding the aqueous phase such as a plasma phase, separated from the oxygen carrier liquid by the separation device in the plasma circulation circuit, to the patient, conveniently by feeding it into the cell-containing fraction before the de-aeration step has been carried out on the cell-containing fraction.

It follows that, in particular, the method may comprise treating human blood, the method including the step of separating blood from the blood circulation circuit into a plasma fraction and a cell-containing fraction, the plasma fraction being fed into the oxygen carrier liquid in the oxygen carrier liquid circulation circuit, and the cell-containing fraction being retained in the blood circulation circuit. In this case, the separation of the plasma fraction and the cell-containing fraction from each other may be by means of a semi-permeable barrier through which the plasma fraction passes and which prevents passage of blood cells therethrough.

In a particular embodiment of the invention the live cells may be liver cells, for example human or porcine liver cells. Thus, the cells may be porcine hepatocytes, which may be obtained from a primary cell culture, or the hepatocytes may be human hepatocytes obtained from a malignant or modified cell line, such as the HUH7 cell line or preferably the HEP-G2 cell line, the cells optionally being co-cultured with parenchymal cells. Thus, in particular the live cells may be selected from the group consisting of porcine hepatocyte cells, human hepatocyte cells, baboon hepatocyte cells and mixtures thereof, the cells treating the blood by performing a synthetic liver function on the blood.

When the apparatus or installation includes a blood circulation circuit connected to a patient and the bio-reactor device contains live cells, the mass of liver cells in the bio-reactor device should preferably be capable of carrying out at least 20% and more preferably at least 30% of the essential liver function required by the patient, and preferably more. Furthermore, oxygen and nutrients should preferably be supplied to the liver cells, and carbon dioxide removed therefrom, at rates adequate to sustain cell viability and cell metabolic activity for a sufficient period to permit liver regeneration or transplantation in the patient, for example 14 days or more. When connected to a patient, in particular, the apparatus or installation is preferably biocompatible and biostable and should preferably minimize any immune response in the patient it will be appreciated that, in this context, the bio-reactor device will act as an artificial organ, namely an artificial liver, which can mimic a patient's normal liver functions, including some possibly unknown functions. In general, the quantity of the liver cells in the matrix through which the oxygen carrier liquid is perfused may be capable of carrying out at least 20%, preferably at least 30% of the essential liver function required by an adult human, oxygen being supplied to the oxygen carrier liquid by an oxygenation device, nutrients being supplied to the oxygen carrier liquid by the blood plasma, carbon dioxide being removed from the oxygen carrier liquid by the oxygenation device, and cell metabolites being removed from the oxygen carrier liquid by the blood plasma, at respective rates which are sufficient for the perfusion of the oxygen carrier liquid through the matrix to sustain viability and metabolic activity of the cells for a period of at least 3 days, preferably at least 7 days and more preferably at least 14 days.

When used as an artificial liver, the bio-reactor device requires the live cells therein to be supplied, inter alia, with oxygen and nutrients, while carbon dioxide and other metabolic by-products are removed therefrom; and at the same time the live cells must be exposed to blood or separated blood fractions such as plasma fractions on which the hepatocyte cells perform their intended metabolic functions, such as the removal therefrom of neurotoxins and hepatic toxins, the production of neurotrophic and hepatotrophic factors, and the production of liver-specific coagulation factors. In this regard the plasma separation device may, for example, provide a semi-permeable barrier such as a membrane, which allows cell-free liquid to pass into the oxygen carrier liquid, but prevents cells from the blood from doing so, and similar considerations apply to the biomass filter and the separation device in the plasma circulation circuit, which may also, for example, provide semi-permeable barriers which allow aqueous cell-free liquid, from which most of the synthetic constituent of the oxygen carrier liquid has been separated, to re-enter the blood circulation circuit. Naturally, other separation devices, such as centrifuges, can be used instead.

Liver cells such as hepatocyte cells are anchorage dependent in that anchorage thereof in a suitable three-dimensional matrix facilitates their growth and cell division, and enhances their functionality as regards metabolic liver functions. The open-cell foam matrix of the present invention provides adequate surface area in a three-dimensional matrix for acceptable cell adhesion and anchorage thereto, which anchorage is effected by the cells themselves; but if the cells are incapable of anchorage in place, or if the anchorage is to be improved, the cells may be encapsulated in a polymeric coating, which may be porous or permeable, the coating being caused or allowed to adhere to the matrix or being integral therewith. Instead, the foam itself may be coated with an anchorage-enhancing substance, such as collagen.

The invention will now be described by way of illustrative, non-limiting example, with reference to the accompanying diagrammatic drawing in which the single FIGURE is a schematic flow diagram of an installation according to the present invention.

BRIEF DESCRIPTION OF DRAWING

In the drawing, reference numeral 10 generally designates a non-portable installation in accordance with the present invention. The primary part of the installation 10 is a bio-reactor device 12 comprising a holder in the form of a reaction vessel or tank 14 provided with a heating/cooling jacket 16 and containing a matrix (shown cross-hatched at 18) of open-cell biocompatible and biostable polyurethane foam. The foam, in the interiors of its cells, contains human hepatocytes (not shown) in a quantity of about $2.5 \times 10^{11}$ cells, ie a quantity amounting normally to 20–30% of that of an average adult liver. The jacket 16 is shown having a low level heating/cooling water inlet flow line 20 and a high level outlet flow line 22, for heating/cooling water. The flow lines 20 and 22 lead to a supply of heating/cooling water(not shown) which is circulated through the jacket 16 by a pump (not shown) at a rate and/or temperature, controlled by a thermostat (also not shown) attached to or in the vessel 14, thereby to control the temperature in the vessel 14 so that it remains at a desired value, namely 37° C., for human hepatocytes.

The bio-reactor device 12 has a high level liquid inlet fed by a pump 24 pumping along flow line 26 at a flow rate of <600 ml/minute, preferably 100–250 ml/minute; and the device 12 has a low level liquid outlet feeding along flow line 28 to a biomass filter 30. Biomass filter 30 has a filter membrane 32 and a biomass outlet feeding along a biomass flow line 32 to waste, and a filtrate outlet feeding along a filtrate flow line 36 to a separation device 38. The device 38 is for separating the liquid phases of an emulsion from each other, namely an aqueous liquid phase from a perfluorocarbon liquid phase, when a perfluorocarbon synthetic oxygen carrier liquid constituent is employed, as described hereunder. When other synthetic oxygen carrier liquid constituents such as dissolved cell-free haemoglobin or suspended liposome-encapsulated haemoglobin are used, separation devices employing other separation techniques will naturally be used.

Figure 1:
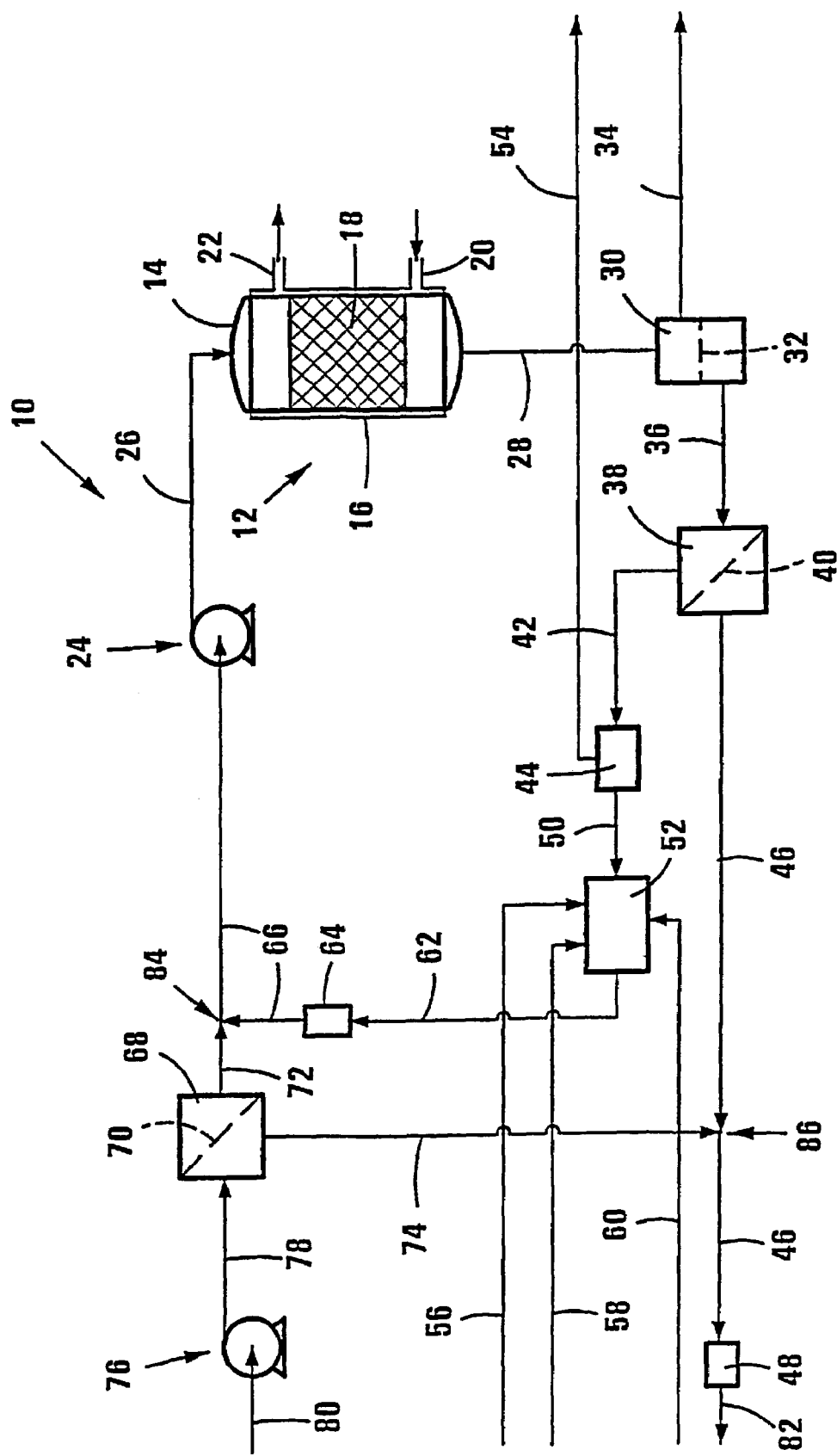

The separation device 38 has a phase separation membrane 40 and has a pair of outlets namely a perfluorocarbon phase outlet to a perfluorocarbon flow line 42 leading to a carbon dioxide removal device 44, and an aqueous or plasma phase outlet to an aqueous or plasma phase flow line 46 leading to a de-aeration device 48. The device 44 has a liquid outlet to a liquid flow line 50 leading to an oxygenation device 52, and a carbon dioxide gas outlet to a carbon dioxide vacuum flow line 54 leading to a vacuum pump (not shown).

The oxygenation device 52 is fed by a nutrient solution feed line 56 and an organic phase make-up flow line 58, also by an oxygen gas feed line 60. The device 52 has a liquid outlet which feeds into a liquid flow line 62 leading to a de-aeration device 64 which in turn has a liquid outlet to a flow line 66 leading to the inlet of the pump 24. A blood-conditioning feed line (not shown) may feed into the device 52, being for feeding blood-conditioning substances to the liquid in the device 52.

The pump 24, bio-reactor 12, filter 30, separation device 38, carbon dioxide removal device 44, oxygenation device 52 and de-aeration device 64, and the flow lines interconnecting them, together form a plasma circulation circuit.

The installation 10 further includes a plasma separation device 68 having a semi-permeable membrane 70. The device 68 has a plasma outlet to plasma flow line 72 leading into line 66, and a cell-containing whole blood outlet to a liquid flow line 74 feeding into line 46, between separation device 38 and de-aeration device 48. Plasma separation device 68 is fed by pump 76 along line 78.

Finally a blood supply line 80 is shown feeding into the inlet of the pump 76, while the de-aeration device 48 is shown having an outlet to a blood return line 82, the lines 80 and 82 leading respectively from and to the veinous system of a patient (not shown), with which veinous system they are in communication. The pump 76, the separation device 68 and the de-aeration device 48, together with the patient and the flow lines interconnecting them, form a blood circulation circuit.

In accordance with the method of the invention, veinous blood is continuously withdrawn from the patient along line 80 by pump 76 at a flow rate of <400 ml/minute, preferably 150–250 ml/minute, which pumps it along line 78 to separation device 68, where it is separated into a whole blood fraction and a plasma fraction. The plasma fraction issues from device 68 at a flow rate of <200 ml/minute, preferably 50–150 ml/minute, along line 72 to meet line 66 at 84 and the whole blood fraction issues along line 74 at a flow rate of <200 ml/minute, preferably 50–150 ml/minute, to meet line 46 at 86. Line 66, where it leaves device 64, contains a perfluorocarbon phase comprising a suitable perfluorocarbon, namely perfluoro-octylbromide in a volumetric concentration of 10–60%. The plasma from device 68 mixes with a pre-formed emulsion comprising perfluorocarbon issuing from device 64 into line 66, the emulsion comprising egg-yolk lecithin as emulsifier, the emulsion having the perfluorocarbon as its disperse phase and the emulsion entering the top of the vessel 14.

In the vessel 14 the emulsion perfuses downwardly through the matrix 18, in contact with the live hepatocyte cells anchored in the matrix. Water flow along lines 20 and 22, to and from jacket 16, controls the temperature of the emulsion in the matrix to substantially 37° C. The hepatocyte cells absorb oxygen and nutrients from the emulsion and the emulsion absorbs carbon dioxide and other metabolic products from the hepatocyte cells. The emulsion leaves the device 12 along line 28 to the biomass filter 30.

In the filter 30 the emulsion is filtered to remove biomass therefrom, the filtered biomass issuing along line 34 from the filter 30 to waste. Filtered emulsion issues from filter 30 along line 36 to separation device 38, where the emulsion is separated into an aqueous or plasma phase and a perfluorocarbon phase. The perfluorocarbon phase leaves device 38 along flow line 42 to carbon dioxide removal device 44, and aqueous or plasma phase leaves device 38 along flow line 46 to de-aeration device 48, the aqueous or plasma phase receiving, at 86, upstream of the device 48, the whole blood from the line 74. Blood comprising said whole blood and said aqueous or plasma phase is de-aerated in de-aeration device 48 and is returned along line 82 to the patient's veinous system.

In the device 44 carbon dioxide is removed under vacuum and discharged along line 54, the perfluorocarbon phase leaving device 44 along line 50 to the oxygenation device 52. Carbon dioxide can, naturally, be removed by other techniques.

In the oxygenation device 52 the perfluorocarbon phase is fed with nutrients along line 56, with perfluorocarbon make-up along line 58 and with oxygen along line 60, perfluorocarbon phase leaving device 52 along line 62 to device 64, where it is de-aerated. Blood-conditioning substances such as pH control substances can also be fed to the perfluorocarbon phase in the device 52 from a feed line (not shown) therefor.

The separation device 68 acts to prevent immunocompetent blood cells from entering the oxygen carrier liquid, to reduce the possibility of an immune activation when immunocompetent cells from the patient come into contact with xenogenic cells in the bio-reactor system.

It is a feature of the invention that separation of the plasma carrier circulation circuit from the blood circulation circuit, allows oxygen carrier liquid to be circulated through the bio-reactor device at a faster rate than blood can be withdrawn from a patient on a continuous basis. In this regard separation device 38 can act as a reservoir for oxygen carrier liquid. A further feature is that the various devices and flow lines should be adequately insulated or temperature-regulated by suitable heating and/or cooling, to preserve a temperature throughout the liquids in the installation as close to 37° C. as is feasible.

It is an advantage of the invention, particularly as illustrated and described with reference to the drawings, that it allows hepatocyte cells to be kept viable while maintaining their metabolic activity for up to 14 days or more. The cells can remove neurotoxins and hepatic toxins from the patient's blood, while producing neurotrophic factors, hepatotrophic factors and liver specific coagulation factors, and while carrying out other hepatocyte metabolic activities. This can, if the device contains a sufficient number of hepatocyte cells, eg 20% or more of the number of such cells in the patient's liver, allow the patient's liver to regenerate, or can sustain the patient for a bridging period until liver transplantation is possible.

The invention claimed is:

1. A bio-reactor device comprising a holder containing a three-dimensional matrix of foam material, the foam material having a porous interior and containing, in its porous interior and anchored thereby, live cells, the bio-reactor device also comprising a liquid contained in the holder, which liquid saturates and immerses the matrix, the matrix being a unitary or integral continuous mass of the foam material, and the device forming part of a liquid circulation circuit arranged for circulation of liquid into the holder, and for circulation thereof out of the holder, wherein the liquid comprises an oxygen-carrier liquid including a synthetic or semi-synthetic oxygen-carrying constituent so that the liquid circulation circuit is an oxygen carrier liquid circulation circuit, the foam material comprises an open-cell foam material, and the circuit is arranged for circulation of the oxygen-carrier liquid by perfusion through the matrix in which the live cells are anchored.

2. A device as claimed in claim 1, in which the open-cell foam material is bio-compatible and bio-stable, being a polymeric foam material.

3. A device as claimed in claim 2, in which the foam material is a foam of a polymer selected from the group consisting of polyurethane polymers, polyvinyl chloride polymers, polyethylene polymers, polypropylene polymers, polystyrene polymers, copolymers of the aforegoing, styrene-butadiene copolymers, styrene-acrylonitrile copolymers, acrylonitrile-butadiene-styrene copolymers, poly(methyl methacrylate) polymers, polyamide polymers, poly (hexamethylene adipamide) polymers, poly(hexamethylene sebacamide) polymers, polycapralactone polymers, poly (ethylene terephthalate) polymers, poly(butylene terephthalate) polymers, polycarbonate polymers, polyacetal polymers, polyvinyl alcohol polymers, urea formaldehyde polymers, fluorine-containing polymers, silicone-containing polymers, and mixtures of the aforegoing polymers and copolymers.

4. A device as claimed in claim 1, in which the live cells are mammalian cells, the oxygen carrier liquid forming a blood substitute which also acts as a carbon dioxide carrier.

5. A device as claimed in claim 1, in which the oxygen carrier liquid comprises an aqueous liquid, the oxygen carrier liquid having, as the synthetic or semi-synthetic oxygen-carrying constituent, at least one member selected from the group consisting of cell-free haemoglobins, cross-linked haemoglobins, liposome-encapsulated haemoglobins and perfluorocarbons.

6. A device as claimed in claim 5, in which the synthetic or semi-synthetic oxygen-carrying constituent is a synthetic perfluorocarbon, the oxygen carrier liquid being an emulsion of an organic phase and an aqueous phase, the organic phase comprising the perfluorocarbon and being the disperse phase of the emulsion, and the aqueous phase being the continuous phase of the emulsion and comprising the aqueous liquid.

7. A device as claimed in claim 5, in which the synthetic or semi-synthetic constituent is a cell-free haemoglobin, the cell-free haemoglobin being dissolved in the aqueous liquid, and the aqueous liquid being blood plasma.

8. A device as claimed in claim 5, in which the synthetic or semi-synthetic constituent is a liposome-encapsulated haemoglobin, the liposome-encapsulated haemoglobin being suspended as a suspension thereof in the aqueous liquid, and the aqueous liquid being blood plasma.

9. A device as claimed in claim 1, in which the holder is a reaction vessel or container having an oxygen carrier liquid inlet and an oxygen carrier liquid outlet, the oxygen carrier liquid outlet being at a lower level than the oxygen carrier liquid inlet and forming an oxygen carrier liquid drain, the holder being provided with a temperature regulation device for regulating the temperature of the matrix and of the oxygen carrier liquid.

10. A device as claimed in claim 1, which forms part of a temperature regulating liquid circuit for circulating a temperature regulating liquid to and away from the holder, the holder being provided with a temperature regulation device in the form of a hollow temperature regulating jacket for the holder, the jacket having an inlet and an outlet for a temperature regulating liquid, the temperature regulating circuit comprising a liquid circulation device for circulating the temperature regulating liquid along and around the temperature regulating circuit, a thermostat, and a heat transfer device remote from the holder and operative in response to signals from the thermostat to control the temperature of the temperature regulating liquid and hence to regulate the temperature of the matrix and of the oxygen carrier liquid.

11. A device as claimed in claim 1, in which the oxygen carrier liquid circulation circuit includes at least one device which is selected from the group consisting of liquid circulation devices for circulating the oxygen carrier liquid along and around the circuit, biomass removal devices for removing biomass from oxygen carrier liquid issuing from the holder, separation devices for separating the synthetic or semi-synthetic constituent of the oxygen carrier liquid from other constituents thereof, carbon dioxide removal devices for removing carbon dioxide from the oxygen carder liquid, oxygenation devices for oxygenating the oxygen carrier liquid, and de-aeration devices for de-aerating the oxygen carrier liquid.

12. A device as claimed in claim 11, in which the circulation circuit includes a plurality of the devices of the group, the devices being arranged, starting with the holder, in a sequence which comprises a single biomass removal device, followed in turn by a single separation device, a single carbon dioxide removal device, a single oxygenation device, a single de-aeration device and a single liquid circulation device, the holder following the liquid circulation device so that the circuit is an endless or closed circuit, and the liquid circulation device being arranged to circulate the oxygen carrier liquid along and around the circuit in the direction in which the devices of the group follow one another in said sequence.

13. A device as claimed in claim 1, in which the oxygen carrier liquid circulation circuit is connected to a blood circulation circuit for circulating blood into contact with oxygen carrier liquid in the oxygen carrier liquid circulation circuit, for delivering cell-free blood constituents to the oxygen carrier liquid circuit, and for receiving or withdrawing cell-free aqueous oxygen carrier liquid constituents from the oxygen carrier liquid circuit, the blood circulation circuit including a blood circulation device for circulating blood along and around the blood circulation circuit, a plasma separation device for separating blood circulating along and around the blood circulation circuit into a cell-free blood plasma fraction and a blood cell-containing fraction containing blood cells and some blood plasma, and a de-aeration device for de-aerating blood circulating along and around the blood circulation circuit.

14. A device as claimed in claim 13, in which the devices of the blood circulation circuit are arranged in a sequence, in which sequence the blood circulation device is followed in turn by the plasma separation device and the de-aeration device, the blood circulation device being arranged to circulate blood along and around the blood circulation circuit in the direction in which the devices of the blood circulation circuit follow one another in said sequence.

15. A device as claimed in claim 13, in which the connection between the oxygen liquid circulation circuit and the blood circulation circuit is a connection between the oxygen carrier liquid circulation circuit and the plasma separation device of the blood circulation circuit.

16. A device as claimed in claim 6, wherein the aqueous liquid comprises blood plasma and is emulsified with the perfluorocarbon.

* * * * *